United States Patent [19]

Morrow et al.

[11] 4,243,681

[45] Jan. 6, 1981

[54] ALKYLTHIOPHENOXYPROPANOLA-MINES AND PHARMACEUTICAL COMPOSITIONS AND USES THEREOF

[75] Inventors: Duane F. Morrow; William L. Matier, both of Evansville, Ind.

[73] Assignee: Mead Johnson & Company, Evansville, Ind.

[21] Appl. No.: 30,497

[22] Filed: Apr. 16, 1979

Related U.S. Application Data

[63] Continuation-in-part of Ser. No. 942,222, Sep. 14, 1978, abandoned, which is a continuation-in-part of Ser. No. 841,168, Oct. 11, 1977, abandoned.

[51] Int. Cl.³ .................. A61K 31/135; C07C 83/00; C07C 91/00; C07C 93/06
[52] U.S. Cl. .................. 424/330; 260/501.17; 564/349
[58] Field of Search ............ 424/330; 260/570.7, 260/570.8, 501.17

[56] References Cited

U.S. PATENT DOCUMENTS

| 3,501,769 | 3/1970 | Crowther et al. | |
|---|---|---|---|
| 3,542,872 | 11/1970 | Koppe et al. | 424/330 |
| 3,542,874 | 11/1970 | Keizer et al. | 424/330 |
| 3,631,108 | 12/1971 | Brandstrom et al. | 260/570.7 |
| 3,740,443 | 6/1973 | Köppe et al. | 424/330 |
| 3,740,444 | 6/1973 | Köppe et al. | 424/330 |
| 3,872,147 | 3/1975 | Köppe et al. | 424/330 |
| 3,873,600 | 3/1975 | Brandstrom et al. | 424/330 |
| 3,925,446 | 12/1975 | Köppe et al. | 424/330 |
| 3,928,601 | 12/1975 | Brandstrom et al. | 424/330 |
| 3,930,016 | 12/1975 | Berntsson et al. | 424/330 |
| 3,937,834 | 2/1976 | Hanger et al. | 424/330 |
| 4,067,904 | 1/1978 | Comer et al. | 424/330 |
| 4,084,002 | 4/1978 | Köppe et al. | 424/330 |

FOREIGN PATENT DOCUMENTS 2551141  5/1977  Fed. Rep. of Germany .

OTHER PUBLICATIONS

J. of Med. Chem., 13, (5), 971–973, (1970), Boissier.

*Primary Examiner*—Douglas W. Robinson
*Attorney, Agent, or Firm*—Robert H. Uloth; Robert E. Carnahan

[57] ABSTRACT

A new class of alkylthiophenoxypropanolamine derivatives and methods for preparation are described. The compounds have vasodilating and antispasmodic activity, inhibit blood platelet aggregation and are substantially free of beta-adrenergic blocking effects. They are particularly valuable in the treatment of disease states responsive to vasodilation such as obstructive peripheral vascular diseases and cerebral vascular deficiencies. A representative and preferred embodiment of the invention consists of 1-[4-(1-methylethylthio)phenoxy]-3-(octylamino)-2-propanol.

15 Claims, No Drawings

ALKYLTHIOPHENOXYPROPANOLAMINES AND PHARMACEUTICAL COMPOSITIONS AND USES THEREOF

CROSS-REFERENCE TO RELATED APPLICATION

This application is a continuation-in-part of co-pending application Ser. No. 942,222 filed Sept. 4, 1978 (now abandoned) which is a continuation-in-part of application Ser. No. 841,168 filed Oct. 11, 1977 (now abandoned).

FIELD OF THE INVENTION

This invention pertains to carbon compounds having drug and bio-affecting properties. It is particularly concerned with new and useful alkylthiophenoxypropanolamines, use thereof in pharmaceutical preparations and therapeutic methods and processes for producing the alkylthiophenoxypropanolamines. The alkylthiophenoxypropanolamines of this invention increase peripheral blood flow, relax vascular smooth muscle, and inhibit platelet aggregation and are considered to be particularly useful in the treatment of obstructive peripheral vascular diseases such as intermittent claudication and cerebro-vascular deficiencies associated with arteriosclerosis.

DESCRIPTION OF THE PRIOR ART

Various alkylthiophenoxypropanolamine modifications have been described and studied in the field of adrenergic agents primarily for the purpose of uncovering more potent and selective beta-adrenergic blocking agents free of unwanted pharmacologic effects. Such compounds are generally considered useful in treating certain forms of hypertension, angina pectoris, heart arrhythmia and pheochromocytoma. Representative of these efforts are compounds described in the following patents and publications.

L. Villa, et al., Il. Farmaco. Sci., Ed. 24, 349–357 (1969) specifically discloses the following alkylthiophenoxypropanolamine compound as part of a structure-activity-relationship study.

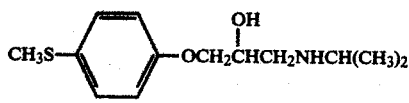

Keizer, et al., U.S. Pat. No. 3,542,874 patented Nov. 24, 1970, discloses 2-(alkylthio)phenoxypropanolamines of the formula

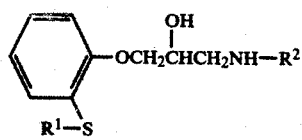

wherein $R^1$ is an alkyl ($C_1$–$C_4$) radical and $R^2$ is inter alia an alkyl ($C_1$–$C_{12}$) or a cycloalkyl ($C_3$–$C_{12}$) radical. This patent teaches that compounds of this type have very effective beta-adrenergic blocking properties. Specific compounds disclosed by Keizer, et al. include those wherein $R^1$ is methyl or ethyl and $R^2$ is isopropyl; $R^1$ is methyl, ethyl, or propyl and $R^2$ is tert.-butyl; $R^1$ is methyl and $R^2$ is cyclopropyl, cyclopentyl, or cyclohexyl; $R^1$ is tert.-butyl and $R^2$ is cyclopentyl.

Crowther, et al., U.S. Pat. No. 3,501,769 patented Mar. 17, 1970 generically discloses compounds of the type

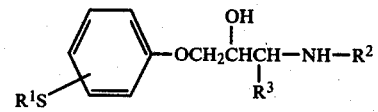

wherein $R^1$ is alkyl (up to 10 C); $R^2$ is alkyl (up to 20 C), cycloalkyl (up to 10 C), etc.; $R^3$ is hydrogen or alkyl (up to 10 C). Notwithstanding the scope of the generic disclosure, Crowther, et al. does not describe a single example of a specific "alkylthio" compound.

Koppe, et al., U.S. Pat. No. 3,872,147 patented Mar. 18, 1975 generically discloses alkylthiophenoxypropanolamines illustrated by the formula

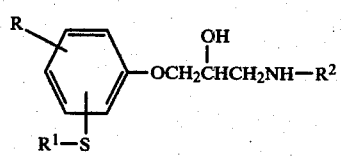

wherein R is alkyl (1–4 C); $R^1$ is alkyl ($C_1$–$C_5$); $R^2$ is alkyl ($C_5$–$C_8$) containing at least one quaternary carbon attached directly through an alkylene chain ($C_1$–$C_4$) to the amino nitrogen atom. None of the specifically disclosed Koppe, et al. compounds, however, constitute an example of an "alkylthiophenoxypropanolamine".

Offenlegungsschrift No. 2,551,141 published May 18, 1977, specifically describes the alkylthiophenoxypropanolamine

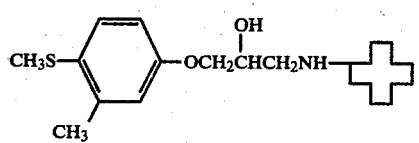

As can be seen from the above prior art, numerous alkylthiophenoxypropanolamines have been generically disclosed but relatively few alkylthiophenoxypropanolamines are specifically described. Compared to the prior art compounds which are reportedly beta-adrenergic blocking agents, the alkylthiophenoxypropanolamines of the present invention are unique in that they reduce vascular resistance with minimal involvement of beta-adrenergic blocking effects.

SUMMARY OF THE INVENTION

Broadly described, the present invention is directed to novel alkylthiophenoxypropanolamines of the formula wherein A, B, and R are independently hydrogen, lower alkyl of 1 to 4 carbon atoms inclusive; $R_1$ is alkyl of 1 to 8 carbon atoms inclusive; $R_2$ is alkyl of 6 to 12 carbon atoms inclusive or cycloalkylalkyl having 5 to 8 ring carbon atoms inclusive attached through an alkylene chain of 2 to 6 carbon atoms inclusive to the amino nitrogen atom; and the pharmaceutically acceptable acid addition salts thereof. This invention is also concerned with pharmaceutical compositions containing the alkylthiophenoxypropanolamines, and further contemplates methods for both producing and employing the compounds and compositions therapeutically.

DETAILED DESCRIPTION OF THE INVENTION

The alkylthiophenoxypropanolamines provided by this invention are represented by formula I

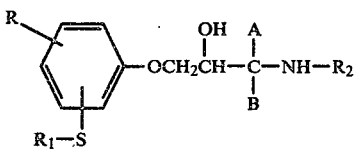

wherein

A, B and R are independently selected from the group consisting of hydrogen and lower alkyl of 1 to 4 carbon atoms inclusive;

$R_1$ is alkyl of 1 to 8 carbon atoms inclusive;

$R_2$ is alkyl of 6 to 12 carbon atoms inclusive or cycloalkylalkyl having 5 to 8 ring carbon atoms inclusive and from 2 to 6 carbon atoms in the alkylene chain, and pharmaceutically acceptable acid addition salts thereof.

As used herein, the term "lower alkyl" refers to a carbon chain comprised of both straight and branched chain carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl.

As used herein, the term "alkyl" refers to straight or branched chain carbon radicals with the number of carbon atoms comprising the particular alkyl radical specifically designated or referred to by standard notations such as ($C_1$–$C_4$), ($C_1$–$C_8$) and ($C_6$–$C_{12}$).

As used herein, the term "cycloalkylalkyl" is intended to refer to a cycloalkyl radical containing from 5 to 8 carbon atoms inclusive (i.e., cyclopentyl, cyclohexyl, cycloheptyl and cyclooctyl) connected to the amino nitrogen atom by an alkylene chain of 2 to 6 carbons. It is to be understood that the "alkylene chain" connecting the cycloalkyl radical to the amino nitrogen atom may be linear or branched.

As used herein, the term "non-toxic pharmaceutically acceptable acid addition salts" refers to salts of compounds of formula I formed with a variety of inorganic and organic acids, the anions of which are relatively non-toxic. Such acid addition salts are considered pharmacologically equivalent to the bases characterized by structural formula I. Examples of useful salt forming acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzenesulfonic, p-toluenesulfonic, and related acids. Acid addition salts of this invention are prepared and isolated by conventional means; for instance, by treating a solution or suspension of the free base in a reaction inert solvent with the desired acid and recovering the salts which form by concentration under reduced pressure or by crystallization techniques or other standard chemical manipulations. Acid addition salts which are somewhat toxic and therefore do not meet the foregoing criteria for pharmacetical acceptability are sometimes useful as intermediates for isolation and purification of the bases of formula I or for other chemical purposes such as separation of optical isomers. Such salts are also considered part of the invention.

As will be apparent to those skilled in the art, the compounds characterized by general formula I have one or more assymmetric carbon atoms and can thus exist as optically active isomers, racemates and diastereoisomers all of which are considered as part of the present invention. The diastereoisomeric mixtures may, depending on physical-chemical differences of the components, be separated into diastereomeric pure racemates by conventional means such as chromatography and/or fractional crystallization. Resolution of racemates of the instant invention to provide optically active isomers of formula I compounds is carried out by conventional resolution methods. For instance, reacting the bases of formula I with optically active acids provides salts thereof from which the enantiomers may be separated by fractional crystallization. Acids suitable for resolving the compounds of formula I are the optically active forms of tartaric acid, di-o-tolyltartaric acid, diacetyltartaric acid, dibenzoyltartaric acid, malic acid, mandelic acid, camphorsulfonic acid, and other optically active acids known to the art. Preferably, the more biologically active optically active stereoisomer is isolated.

Contemplated sub-classes within the ambit of formula I which further characterize the alkylthiophenoxypropanolamines of the invention are compounds of formula I wherein (Ia) A, B and R are hydrogen and substituents $R_1$ and $R_2$ are as previously defined for formula I;

(Ib) A, B and R are hydrogen, $R_1$ is methyl and substituent $R_2$ is as previously defined for formula I;

(Ic) A, B and R are hydrogen, $R_1$ is methyl and substituent $R_2$ is ($C_6$–$C_{12}$) alkyl;

(Id) A, B and R are hydrogen, $R_1$ is lower ($C_1$–$C_4$) alkyl and $R_2$ is ($C_6$–$C_{12}$) alkyl;

(Ie) A, B and R are hydrogen, $R_1$ is ($C_1$–$C_8$) alkyl and $R_2$ is ($C_6$–$C_{12}$) alkyl;

(If) A, B and R are hydrogen, $R_1$ is isopropyl and substituent $R_2$ is as previously defined for formula I;

(Ig) A, B and R are hydrogen, $R_1$ is isopropyl and $R_2$ is ($C_6$–$C_{12}$) alkyl;

(Ih) A, B and R are hydrogen, $R_1$ is ($C_1$–$C_8$) alkyl and $R_2$ is n-octyl;

(Ii) A, B and R are hydrogen, $R_1$ is ($C_1$–$C_4$) alkyl and $R_2$ is n-octyl;

(Ij) A, B and R are hydrogen, $R_1$ is ($C_1$–$C_8$) alkyl with the $R_1$S radical in the para-position and $R_2$ is ($C_6$–$C_{12}$) alkyl;

(Ik) A, B and R are hydrogen, $R_1$ is ($C_1$–$C_4$) alkyl with the $R_1$S radical in the para-position and $R_2$ is ($C_6$–$C_{12}$) alkyl;

(Il) A, B and R are hydrogen, $R_1$ is ($C_1$–$C_4$) alkyl with the $R_1$S radical in the para-position and $R_2$ is n-octyl;

(Im) A, B and R are hydrogen, $R_1$ is ($C_1$–$C_8$) alkyl with the $R_1$S radical in the ortho-position and $R_2$ is ($C_6$–$C_{12}$) alkyl;

(In) A, B and R are hydrogen, $R_1$ is $(C_1-C_4)$ alkyl with the $R_1S$ radical in the ortho-position and $R_2$ is n-octyl;

(Io) A and B are hydrogen, R is $(C_1-C_4)$ alkyl in the ortho-position, and $R_2$ is n-octyl;

(Ip) A and R are hydrogen, B is $(C_1-C_4)$ alkyl, $R_1$ is $(C_1-C_4)$ alkyl with the $R_1S$ radical in the para-position, and $R_2$ is $(C_6-C_{12})$ alkyl;

(Iq) A and R are hydrogen, B is $(C_1-C_4)$ alkyl, $R_1$ is $(C_1-C_4)$ alkyl with the $R_1S$ radical in the para-position, and $R_2$ is n-octyl;

(Ir) A and R are hydrogen, B is methyl, $R_1$ is $(C_1-C_8)$ alkyl and $R_2$ is $(C_6-C_{12})$ alkyl;

(Is) A and R are hydrogen, B is methyl, $R_1$ is $(C_1-C_8)$ alkyl and $R_2$ is n-octyl.

(It) A, B and R are independently hydrogen or lower $(C_1-C_4)$ alkyl, $R_1$ is $(C_1-C_8)$ alkyl with the R,S radical in the para-position and $R_2$ is $(C_5-C_8)$ cycloalkyl attached through an alkylene chain of 2 to 6 carbon atoms inclusive to the amino nitrogen atom;

(Iu) A, B and R are hydrogen, $R_1$ is $(C_1-C_8)$ alkyl with the $R_1S$ radical in the para-position and $R_2$ is $(C_5-C_8)$ cycloalkyl attached through an alkylene chain of 2 to 6 carbon atoms inclusive to the amino nitrogen atom, (Iv) A, B and R are hydrogen, $R_1$ is $(C_1-C_8)$ alkyl with the $R_1S$ radical in the meto-position and $R_2$ is $(C_6-C_{12})$ alkyl, (Iw) A, B and R are hydrogen, $R_1$ is $(C_1-C_4)$ alkyl with the $R_1S$ radical in the meta-position and $R_2$ is n-octyl.

According to a feature of the present invention, there is provided a process for preparing those alkylthiophenoxypropanolamines of formula I wherein A and B are limited to hydrogen which comprises reacting an alkylthiophenol derivative of formula II

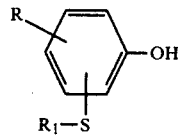

(II)

wherein R and $R_1$ have meanings hereinabove described with an epihalohydrin of formula II

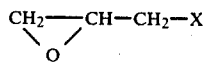

(III)

wherein X signifies halogen, preferably chlorine or bromine, and condensing the epihalohydrin reaction product with an amine of formula IV

 $H_2N-R_2$ (IV)

wherein $R_2$ has the meaning hereinabove described; whereafter, if desired, the formula I product in free base form is reacted with an acid to form an acid addition salt thereof.

The required formula II alkylthiophenols are obtained by coupling a diazotized aminophenol with an alkyl mercaptan to form a diazosulfide which is then decomposed providing the corresponding alkylthiophenol. This is a conventional method and adaptations thereof are described in R. B. Wagner, and H. D. Zook, *Synthetic Organic Chemistry*, page 789 (1953 Wiley); E. Miller, et al., J. Am. Chem. Soc., 55, 1224 (1933); S. Asaka, et al., Chem. Abrs. 61, 13243a.

Suitable Alkylthiophenol reactants of formula II which may be employed in the present process include:
4-methylthiophenol,
4-ethylthiophenol,
4-n-propylthiophenol,
4-n-butylthiophenol,
4-n-pentylthiophenol,
4-n-hexylthiophenol,
4-n-heptylthiophenol,
4-n-octylthiophenol,
4-isopropylthiophenol,
4-(3-methylbutylthio)phenol,
2-n-butylthiophenol,
3-n-butylthiophenol,
2-ethylthiophenol,
2-n-propylthiophenol,
2-isopropylthiophenol,
3-ethylthiophenol,
3-n-propylthiophenol,
3-isopropylthiophenol,
2-methyl-4-(methylthio)phenol,
3-methyl-4-(methylthio)phenol.

Suitable amines of formula IV which may be employed in the present process include:
n-hexylamine,
n-heptylamine,
n-octylamine,
n-nonylamine,
n-decylamine,
n-undecylamine,
n-dodecylamine,
isooctylamine,
2,2-dimethylhexylamine,
1,1-dimethylheptylamine.

Inasmuch as an epihalohydrin molecule of formula III has two reactive positions, reaction with an alkylthiophenol of formula II may yield a mixture of formulas V and VI reaction products wherein R, $R_1$ and X are as defined above.

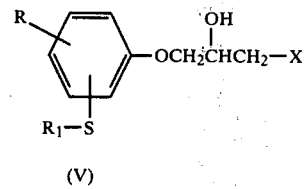

(V)

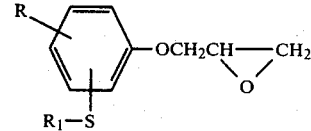

(VI)

During the further course of the process, however, the two possible intermediates of formula V and formula VI on condensation with a formula IV amine yield the same final alkylthiophenoxypropanolamine product. Consequently, it is not necessary to effect a separation of any mixtures of intermediates of formulas V and VI which may result from interaction of a formula II phenol with a formula III epihalohydrin. Under the reaction conditions employed in the instant process, the epoxides of formula VI are preferentially formed.

If desired, the epihalohydrin reaction product may be taken up in an inert solvent such as chloroform and shaken with excess concentrated hydrochloric acid to convert epoxides of formula VI into the corresponding formula V alkylthiophenoxy-halohydrin. Conversely, if desired, the halohydrins of formula V may be converted to the corresponding formula VI by a conventional methods, e.g., by treatment with base according to the procedure of O. Stephenson, J. Chem. Soc., 1574 (1954).

The interaction of formula II phenols with formula III epihalohydrins is carried out in the presence of a sufficient amount of a dilute aqueous alkaline metal hydroxide such as sodium hydroxide to neutralize the acidic phenolic group at temperatures in the range of 0°–100° and preferably 25°–35° according to the procedure of Y. M. Beasley, et al., J. Pharm. Pharmacol., 10, 47–59 (1958).

Alternatively, the interaction of formula II phenols with formula III epihalohydrins can also be effected with catalysts such as N-benzylisopropylamine hydrochoride, pyrrolidine, pyridine, piperidine, piperidine acetate, piperidine hydrochloride, and the like with an excess of epihalohydrin.

The condensation of the epihalohydrin reaction product of formula V or VI with a formula IV amine is carried out preferably in organic solvent inert under the reaction conditions. Suitable solvents include methanol, ethanol, butanol, hexanol, toluene, dioxane, tetrahydrofuran, dibutylether, dimethoxyethane, ethylene glycol. The condensation can also be effected in the absence of a reaction solvent with equimolar amounts of the reactants.

Another feature of the present invention involves an alternate method for producing compounds of formula I wherein A and B are limited to hydrogen which comprises reacting a formula II phenol with a compound of formula VII in alkaline medium

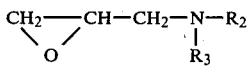

to provide a compound of formula VIII

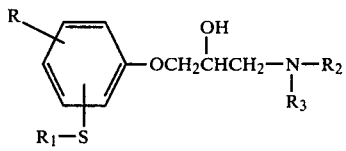

wherein R, $R_1$ and $R_2$ have the same meaning as in formula I and $R_3$ stands for hydrogenolysable radical such as benzyl or benzhydryl; and converting said compound of formula VIII to an alkylthiophenoxy-propanolamine of formula I. Removal of the hydrogenolysable blocking group may be effected by catalytic hydrogenation, for example by hydrogenation in the presence of palladium-on-charcoal catalyst, in an inert solvent, e.g., ethanol or aqueous ethanol.

The compounds of formula VII may be obtained according to known methods. For example, 1-[(N-benzyl)-n-octylamino]-2,3-epoxypropane is obtained by reaction of N-benzyl-n-octylamine and epichlorohydrin in alkaline medium (e.g., aqueous potassium hydroxide) according to the method described by L. Villa, et al., Farmaco., Ed. Sci., 24(3), 349–357 (1969).

A further feature of the invention is directed to a method for producing compounds of formula I wherein A, B, and R are independently selected from the group consisting of hydrogen and lower ($C_1$–$C_4$) alkyl, $R_1$ is ($C_1$–$C_8$) alkyl, and $R_2$ is ($C_6$–$C_{12}$) straight or branched chain alkyl with the carbon atom thereof attached through a divalent methylene (i.e. —$CH_2$—) radical to the amino nitrogen atom or ($C_5$–$C_8$) cycloalkyl attached through an alkylene chain of 2 to 6 carbon atoms inclusive wherein said alkylene chain is attached through a divalent methylene (i.e. —$CH_2$—) radical to the amino nitrogen atom which comprises sequential steps of reducing a compound of formula IX

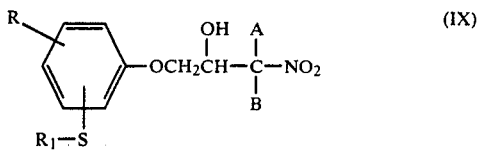

wherein A, B, R and $R_1$ are as defined to provide the primary amino compound X

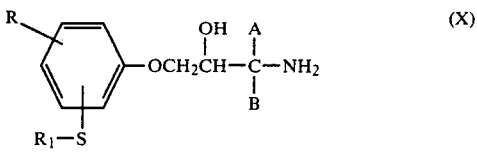

wherein A, B, R and $R_1$ are as defined, and reductively alkylating a compound of formula X with an aldehyde of formula XI

wherein Y is straight or branched chain alkyl of 5 to 11 carbon atoms inclusive or cycloalkylalkyl having 5 to 8 ring carbon atoms and 1 to 5 carbon atoms in the alkylene chain.

The nitro alcohols of formula IX are obtained by an aldol-type condensation of appropriate nitroalkanes and aldehydes in the presence of base or by condensation of the sodium salt of the nitro alkane with sodium bisulfite addition products of the aldehyde in the presence of a trace of alkali or weak acid. Alkylthiophenoxy aldehyde starting materials are obtained by reacting the appropriate alkylthiophenol with the diethylacetal of bromoacetaldehyde followed by acid catalyzed hydrolysis of the acetal groups.

As stated hereinabove, the alkylthiophenoxy-propanolamines of the present invention increase peripheral blood flow, relax vascular smooth muscle, and inhibit platelet aggregation. The compounds are substantially free of beta-adrenergic blocking effects which inhibit peripheral vasodilating activity of beta-adrenergic stimulatory endogenous amines. Standard in vivo and in vitro pharmacological test methods can be employed in assessing the activity of compounds characterized by formula I. Among such tests considered useful are the perfused dog hind limb preparation (vasodilator action), the spasmogen-challanged rabbit aortic strip (antispasmodic activity) and inhibition of adenosine diphosphate and collagen-induced platelet aggregation in human platelet-rich plasma (antithrombogenic action). The isoproterenol challenged guinea pig trachea test, which is standard in the art, is suitable for measuring beta-adrenergic blocking action.

In addition to having vasodilating, antispasmodic and inhibition of blood platelet aggregation properties, some of the compounds of Formula I inhibit lipolysis (as shown in the rat epidimal fat pad lipolysis model) and cholesterol biosynthesis. Compounds of this type are of value as hypocholesterolemic agents.

Another aspect of the instant invention concerns a therapeutic process for treating a mammal requiring vasodilation which comprises systemically administering to the mammal an effective vasodilating amount of a compound selected from the group characterized by formula I and pharmaceutically acceptable non-toxic acid addition salt thereof.

As used herein, the term "effective vasodilating amount" is construed to mean a dose which exerts a vasodilator effect in the effected mammal without untoward side effects.

By systemic administration, it is intended to include both oral and parenteral routes. Examples of parenteral administration are intramuscular, intravenous, intraperitoneal, rectal, and subcutaneous administration. In rectal administration, both ointments and suppositories may be employed. While the dosage will vary to some extent with the mode of administration and the particular compound chosen, from about 0.5 mg. per kg. body weight to 25 mg. per kg. body weight of a compound characterized by formula I or non-toxic pharmaceutically acceptable salts thereof administered in effective single or multiple dosage units generally provides the desired vasodilating effect.

In carrying out the therapeutic process of the instant invention, the formula I compounds are generally administered for vasodilating purposes in the form of a pharmaceutical preparation containing either a formula I free base or a pharmaceutically acceptable non-toxic acid addition salt thereof as the active component in combination with a pharmaceutically acceptable carrier. The carrier may be solid, semi-solid, liquid diluent or a capsule. Accordingly, a further feature of the instant invention is directed to pharmaceutical compositions containing the compounds of formula I or non-toxic pharmaceutically acceptable acid addition salts thereof in combination with a pharmaceutically acceptable carrier.

For the preparation of pharmaceutical compositions containing the compounds of formula I in the form of dosage units for oral administration, the compound is mixed with a solid, pulverulent carrier, (e.g. lactose, sucrose, sorbitol, mannitol, potato starch, corn starch, amylopectin, cellulose derivatives, or gelatin) as well as with an anti-friction agent (e.g. magnesium stearate, calcium stearate, polyethylene glycol waxes or the like) and pressed into tablets. The tablets may be used uncoated or coated by conventional techniques to delay disintegration and absorption in the gastrointestinal tract thereby providing a sustained action over a longer time period. If coated tablets are wanted, the above prepared core may be coated with concentrated solution of sugar, which solution may contain e.g. gum, arabic, gelatin, talc, titanium dioxide, or the like. Furthermore, tablets may be coated with a lacquer dissolved in an easily volatile organic solvent or mixture of solvents. If desired, dye may be added to this coating.

In the preparation of soft gelatin capsules or in the preparation of similar closed capsules, the active compound is mixed with a vegetable oil. Hard gelatin capsules may contain granules of the active ingredient in combination with a solid, pulverulent carrier such as lactose, saccharose, sorbitol, starch, (e.g., potato starch, corn starch, or amylopectin), cellulose derivatives or gelatin.

Dose units for rectal administration may be prepared in the form of suppositories containing the active substance of formula I in mixture with a neutral fat base, or they may be prepared in form of gelatin-rectal capsules containing the active substance in a mixture with a vegetable oil or paraffin oil.

Liquid preparations for oral administration may be present in the form of elixirs, syrups or suspensions containing from about 0.2% by weight to about 20% by weight of the active ingredient. Such liquid preparations may contain coloring agents, flavoring agents, sweetening agents, and carboxymethylcellulose as a thickening agent.

Suitable solutions for parenteral administration by injection may be prepared as an aqueous solution of a water-soluble pharmaceutically acceptable salt of the compounds of formula I adjusted to a physiologically acceptable pH. These solutions may also contain stabilizing agents.

Pharmaceutical tablets for oral use are prepared by conventional method involving mixing the therapeutic compound of formula I and necessary axillary agents.

Specific alkylthiophenoxypropanolamines of the invention are those hereinafter described in the examples. Of these, compounds particularly preferred for their vasodilating properties and absence of significant beta-adrenergic blocking activity are:

1-[4-(methylthio)phenoxy]-3-(octylamino)-2-propanol,
1-[4-[(1-methylethyl)thio]phenoxy]-3-(octylamino)-2-propanol,
1-[3-[(1-methylethyl)thio]phenoxy]-3-(octylamino)-2-propanol,
1-[4-[(1-methylethyl)thio]phenoxy]-3-(dodecylamino)-2-propanol,
1-[(2-cyclohexylethyl)amino]-3-[4-[(1-methylethyl)thio]phenoxy]-2-propanol,
1-[(4-cyclohexylbutyl)amino]-3-[4-[(1-methylethyl)thio]phenoxy]-2-propanol,
1-[2-methyl-4-(methylthio)phenoxy]-3-(octylamino)-2-propanol,
1-[2-(methylthio)phenoxy]-3-(octylamino)-2-propanol.

The following examples illustrate but do not limit the scope of the invention. All temperatures expressed herein are in degrees centigrade.

EXAMPLE 1

1-[4-(Methylthio)phenoxy]-3-(octylamino)-2-propanol

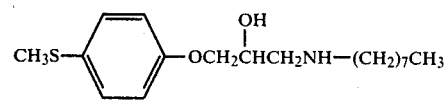

A solution of 4-(methylthio)phenol (5,6 g., 0.04 moles) and sodium hydroxide (2.4 g., 0.06 moles) in 50 ml. of water is treated with epichlorohydrin (7.4 g., 0.08 moles). The resulting mixture is first stirred at 30°–35° for 24 hr. and then extracted with chloroform. After washing the chloroform extract with water and drying over magnesium sulfate, distillables are removed under reduced pressure to provide the epichlorohydrin derivative 1-(4-methylthio)phenoxy-2,3-epoxypropane which is taken up in 30 ml. of ethanol, treated with n-octylamine (7.5 g., 0.06 mole) and refluxed for a period of 4 hr. Concentration of the reaction mixture under reduced pressure to about one-half volume provides a white solid which is collected and crystallized from ethanol to afford a 21% yield of analytically pure 1-[4-(methylthio)phenoxy]-3-(octylamino)-2-propanol, m.p. 79.5°–80.5° (corr.).

Anal. Calcd. for $C_{18}H_{31}NO_2S$: C, 66.42; H, 9.60; N, 4.30; S, 9.85. Found: C, 66.30; H, 9.69; N, 4.13; S, 9.58.

EXAMPLE 2

1-[4-[(1-Methylethyl)thio]phenoxy]-3-(octylamino)-2-propanol Hydrochloride

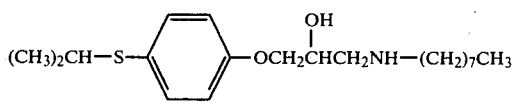

(a) 4-(Isopropylthio)phenol.—A solution of sodium nitrite (113.8 g., 1.65 mole) in 210 ml. of water is added to a stirred solution of p-aminophenol (163.7 g., 1.5 mole) in 825 ml. of 4 N hydrochloric acid at −5°. After stirring for an additional 2 hr. period at −5°, the solution of the diazotized phenol is added over a 45 min. period to a previously prepared cold (−5°) solution of sodium hydroxide (270.6 g., 6.77 moles) and 2-propanethiol (126.4 g., 1.66 moles) in 525 ml. of water with the reaction maintained under a nitrogen atmosphere. When addition is complete, the mixture is permitted to warm to 27° and is kept at that temperature for a period of 16 hr. Then, the mixture is cooled to 0° and acidified with 570 ml. of 12 N hydrochloric acid. Excess 2-propanethiol is removed by bubbling nitrogen gas through the acidified solution into a permanganate trap for a 2 hr. period. The resulting solution is extracted with several portions of dichloromethane and the combined extracts washed with water, dried over magnesium sulfate containing charcoal and filtered. Concentration of the filtrate under reduced pressure provides a residual oil which is distilled affording 81 g. (32% yield) of 4-(isopropylthio)phenol, b.p. 114°–123° (1.2 mm Hg).

(b) A solution of 4-(isopropylthio)phenol, (6.6 g., 0.04 mole) and sodium hydroxide (2.6 g., 0.065 mole) in 50 ml. of water is treated with epichlorohydrin (7.4 g., 0.08 moles). The resulting mixture is first stirred at 30°–35° for 24 hr. and then extracted with chloroform. After washing the chloroform extract with water and drying over magnesium sulfate, distillables are removed under reduced pressure to provide the epichlorohydrin intermediate 1-(4-isopropylthiophenoxy)-2,3-epoxypropane. The epichlorohydrin intermediate is taken up in 30 ml. of ethanol, treated with n-octylamine (7.5 g., 0.06 mole) and refluxed for a period of 4 hr. Concentration of the reaction mixture under reduced pressure affords a residue which is taken up in ethanol and treated with 6 ml. of 12 N hydrochloric acid. Concentration of the acidified solution under reduced pressure and crystallization of residual material from ethanol provides an analytically pure (20% yield) (1-[4-[(1-methylethyl)thio]-phenoxy]-3-(octylamino)-2-propanol hydrochloride, m.p. 171°–173°–186.5° (corr.) (double melting point).

Anal. Calcd. for $C_{20}H_{35}NO_2S.HCl$. C, 61.59; H, 9.30; N, 3.59; S, 8.22; Cl, 9.09. Found: C, 61.68; H, 9.29; N, 3.47; S, 8.15; Cl, 9.15.

EXAMPLE 3

1-[3-[(1-Methylethyl)thio]phenoxy]-3-(octylamino)-2-propanol Hydrochloride

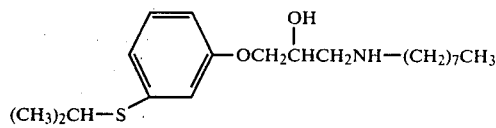

Reaction of the epichlorohydrin derivative of 3-(isopropylthio)phenol (4.85 g., 0.029 mole) with n-octylamine (4 g., 0.031 mole) according to the procedure of Example 2(b) and crystallization of the crude product from ethanol-ether affords a 13% yield of analytically pure 1-[3-[(1-methylethyl)thio]phenoxy]-3-(octylamino)2-propanol hydrochloride, m.p. 125°–127° (corr.).

Anal. Calcd. for $C_{20}H_{35}NO_2S.HCl$: C, 61.59; H, 9.30; N, 3.59. Found: C, 61.22; H, 9.09; N, 3.53.

EXAMPLE 4

1-[4-[(1-Methylethyl)thio]phenoxy]-3-(dodecylamino)-2-Propanol Hydrochloride

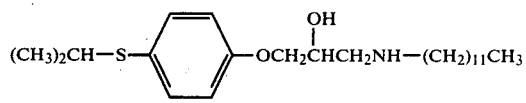

Reaction of the epichlorohydrin derivative of 4-(isopropylthio)phenol (15.7 g., 0.07 mole) with n-dodecylamine (13.9 g., 0.075 mole) according to the procedure of Example 2(b) and crystallization of the crude product from methanol affords a 13% yield of analytically pure 1-[4-[(1-methylethyl)thio]phenoxy]-3-dodecylamino)-2-propanol hydrochloride, m.p. 153.5°–156.6°–190.5° (corr.) (double melting point).

Anal. Calcd. for $C_{24}H_{43}NO_2S.HCl$: C, 64.61; H, 9.94, N, 3.14. Found: C, 64.38; H, 10.07; N, 2.97.

EXAMPLE 5

1-[(2-Cyclohexylethyl)amino]-3-[4-(1-methylethyl)thio]phenoxy]-2-propanol Hydrochloride

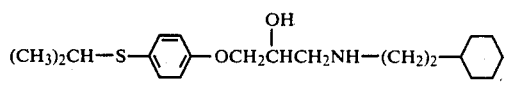

Reaction of the epichlorohydrin derivative of 4-(isopropylthio)phenol (5.0 g., 0.022 mole) with cyclohexylethylamine (3.3 g., 0.026 mole) according to the procedure of Example 2(b) and crystallization of the crude product from isopropyl alcohol affords an 18% yield of analytically pure 1-[(2-cyclohexylethyl)amino]-3-[4-[(1-methylethyl)thio]phenoxy]-2-propanol hydrochloride, m.p. 180°–182° (corr.).

Anal. Calcd. for $C_{20}H_{33}NO_2S.HCl$: C, 61.91; H, 8.83; N, 3.61. Found: C, 61.73; H, 8.71; N, 3.88.

EXAMPLE 6

1-[(4-Cyclohexylbutyl)amino]amino]-3-[4-[(1-methylethyl)thio]phenoxy]-2-propanol Hydrochloride

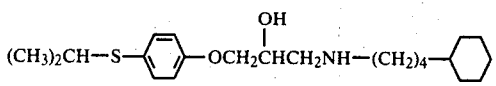

Reaction of the epichlorohydrin derivative of 4-(isopropylthio)phenol (9.0 g., 0.04 mole) with cyclohexylbutylamine (6.7 g., 0.043 mole) according to procedure of Example 2(b) and crystallization of the crude product from ethanol affords an 11.4% yield of analytically pure 1-[(4-cyclohexylbutyl)amino]-3-[4-[(1-methylethyl)thio]phenoxy]-2-propanol hydrochloride, m.p. 179° with prior softening from 118°.

Anal. Calcd. for $C_{22}H_{37}NO_2S.HCl$: C, 63.51; H, 9.20; N, 3.37. Found: C, 63.46; H, 9.35; N, 3.29.

EXAMPLE 7

1-[2-Methyl-4-(methylthio)phenoxy]3-(octylamino)-2-propanol

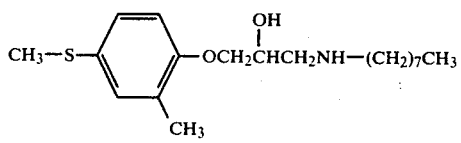

The epichlorohydrin derivative of 2-methyl-4-(methylthio)phenol (3.14 g., 0.015 mole) is reacted with n-octylamine (1.93 g. 0.015 mole) according to the procedure of Example 1. Concentrating the reaction mixture and crystallization of residual material from ethylacetate-hexane affords a 19% yield of analytically pure 1-[2-methyl-4-(methylthio)phenoxy]-3-(octylamino)-2-propanol, m.p. 59°-60° (corr.).

Anal. Calcd. for $C_{19}H_{33}NO_2S$: C, 67.21; H, 9.80; N, 4.13. Found: C, 66.80; H, 9.92; N, 3.81.

EXAMPLE 8

1-[2-(Methylthio)phenoxy]-3-(octylamino)-2-propanol Hydrochloride

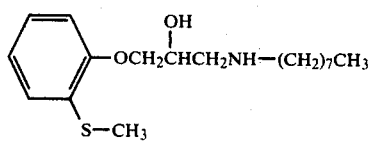

Reaction of the epichlorhydrin derivative of 2-(methylthio)phenol (14 g., 0.071 mole) with n-octylamine (9.04 g., 0.07 mole) according to the procedure of Example 2(b) and crystallization of the crude product from methanol-ether affords an 18% yield of analytically pure 1-[2-(methylthio)phenoxy]-3-(octylamino)-2-propanol hydrochloride, m.p. 105.5°-107.5° (corr.).

Anal. Calcd. for $C_{18}H_{31}NO_2S.HCl$: C, 59.73; H, 8.91; N, 3.87. Found: C, 59.86; H, 9.07; N, 3.71.

EXAMPLE 9

1-[4-[(1-Methylethyl)thio]phenoxy]-3-[(2,2-dimethyl-1-hexyl)amino]-2-propanol

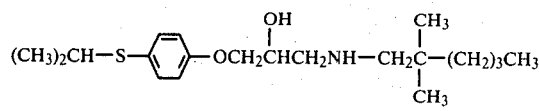

(a) 2,2-Dimethylhex-1-ylamine. A solution of capronitrile (25 g., 0.26 mole) and methyl iodide (75 g., 0.53 mole) in 80 ml. of dry toluene is warmed to 80° and treated gradually with a suspension of sodium amide (25.4 g., 0.65 mole) in 100 ml. of toluene at a rate sufficient to maintain general reflux. After addition is complete, the mixture is stirred and refluxed for an additional 2 hr. period, cooled and treated with 150 ml. of water. The organic layer is separated, washed with water and dried over magnesium sulfate. Concentration of the dried solution under reduced pressure and distillation of residual material affords an 81% yield of 2,2-dimethylcapronitrile.

A solution of 2,2-dimethylcapronitrile (10.0 g., 0.078 mole) in 100 ml. of ether is added slowly to a suspension of lithium aluminum hydride (6.0 g., 0.158 mole) in 200 ml. of ether while maintaining the reaction at 0°-5°. After stirring the reaction mixture for an additional 2 hr. at 0.5°, the mixture is hydrolyzed by sequentially adding 6.0 ml. of water, 6.0 ml. of 15% sodium hydroxide solution, and finally 18 ml. of water. The hydrolyzed mixture is stirred for an additional hour, filtered and the ether phase concentrated under reduced pressure. Distillation of residual material provides 2,2-dimethylhex-1-ylamine.

(b) Reaction of the epichlorohydrin derivative of 4-(isopropylthio)phenol with 2,2-dimethylhex-1-ylamine according to the procedure of Example 2(b) and conversion of the free base to the hydrochloride provides 1-[4-[(1-methylethyl)thio]phenoxy]-3-[(2,2dimethyl-1-hexylamino]-2-propanol hydrochloride.

EXAMPLE 10

1-[4-[(1-Methylethyl)thio]phenoxy]-3-[(2-methyl-2-octyl)amino]-2-propanol

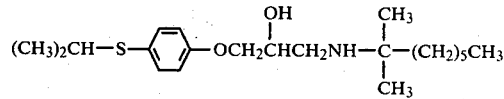

(a) 2-Methyl-2-octanol. A solution of methylheptanoate (14.5 g., 0.1 mole) in 200 ml. of ether is added to 200 ml. of 3 $\underline{M}$ solution (0.6 mole) of methyl magnesium bromide in ether at a rate sufficient to maintain refluxing. After addition is complete, the resulting mixture is refluxed for 1 hr. and then stirred at 26° for a 16 hour period. The mixture is hydrolyzed by the addition of dilute ammonium chloride solution, filtered and the filter cake dissolved in 2 $\underline{N}$ hydrochloric acid and extracted with ether. The ethereal extract and filtrate are combined, sequentially washed with water, dilute sodium bicarbonate solution and brine and dried over magnesium sulfate. Concentration of the dried solution and distillation of residual material under reduced pressure provides 13.1 g. (91% yield) of 2-methyl-2-octanol, b.p. 130° (100 mm Hg).

(b) N-(2-Methyl-2-octyl)acetamide. A solution of concentrated sulfuric acid (5.55 g., 0.055 mole) in 32 ml. of glacial acetic acid is treated with acetonitrile (2.5 g., 0.016 mole) and 2-methyl-2-octanol (8.0 g., 0.055 mole) and the resulting mixture stirred at 26° for a 17 hr. period. After diluting with 125 ml. of water, the mixture is extracted with ether and the ethereal extract sequentially washed with water, dilute sodium bicarbonate solution and brine and dried over magnesium sulfate. Concentration of the dried solution provides 8.7 g. (85% yield) of N-(2-methyl-2-octyl)acetamide which is used in the next step without further purification.

(c) 2-Methyl-2-octylamine. A solution of potassium hydroxide (10.0 g., 0.18 mole) in 100 ml. of ethylene glycol is treated with N-(2-methyl-2-octyl)acetamide (13.0 g., 0.07 mole) and the mixture heated at 200° for a 64 hr. period. The reaction mixture is diluted with 400 ml. of water and extracted with ether. The ethereal extract is washed with water and brine and then dried over sodium sulfate. Concentration of the dried solution under reduced pressure affords 10.4 g. (62% yield) of 2-methyl-2-octylamine which is used in the next step without further purification.

(d) 1-[4-[(1-Methylethyl)thio]phenoxy]-3-[(2-methyl-2-octyl)amino]-2-propanol Preparation. A solution of the epichlohydrin derivative of 4-(isopropylthio)phenol (7.8 g., 0.035 mole) and 2-methyl-2-octylamine (5.0 g., 0.035 mole) in 100 ml. of ethanol is refluxed for a 17 hr. period. The reaction mixture is concentrated under reduced pressure and residual material heated at 80° (0.5 mm Hg) to remove residual excess reagents. The crude free base is treated with 6 N hydrochloric acid to provide the hydrochloride salt which crystallized from ether-hexane affords 3.0 g. (21% yield) of 1-[4-[(1-methylethyl)thio]phenoxy]-3-[(2-methyl-2-octyl)amino]-2-propanol hydrochloride, m.p. 165°.

EXAMPLE 11

3-Methyl-1-[4-[(1-methylethyl)thio]phenoxy]-3-(octylamino)-2-butanol

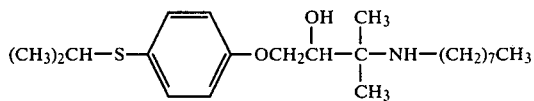

(a) Diethylacetyl of 4-[(1-methylethyl)thio]phenoxyacetaldehyde

A solution of 4-[(1-methylethyl)thio]phenol (24.2 g., 0.144 mole) in 180 ml. of 2-ethoxyethanol is treated with 7.2 g. of a 50% dispersion of sodium hydride in mineral oil and the mixture stirred until hydrogen evolution ceases. The diethylacetal of bromoacetaldehyde (30.0 g., 0.152 mole) is added to the reaction mixture which is then stirred and refluxed for a 19 hr. period, cooled, diluted with water and extracted with ether. Ether extracts are combined, washed with water, dried over magnesium sulfate, and concentrated under reduced pressure to an oil. Distillation of residual oil under reduced pressure provides 28.1 g., (69% yield) of the diethylacetal of 4-[(1-methylethyl)thio]phenoxyacetaldehyde, b.p. 142°–146° (0.07 mm Hg).

(b) 4-[(1-Methylethyl)thio]phenoxyacetaldehyde. A solution of the diethylacetal of 4-[(1-methylethyl)thio]phenoxyacetaldehyde (10 g., 0.035 mole) in 100 ml. of aqueous ethanol (60:40) is treated with 5 ml. of 6 N hydrochloric acid and the resulting mixture refluxed for a period of 2 hr. The cooled mixture is partitioned between ether and water and the ethereal phase washed with water and brine and then dried over magnesium sulfate. Concentration of the dried ethereal solution under reduced pressure and distillation of residual material affords 4-[(1-methylethyl)thio]phenoxyacetaldehyde.

(c) 3-Methyl-1-[4-[(1-methylethyl)thio]phenoxy]-3-nitro-2-butanol. A solution of 2-nitropropane (1.8 g., 0.02 mole) and 1.0 g. of sodium hydroxide in 10 ml. of water is added to a stirred suspension of 4-[(1-methylethyl)thio]phenoxyacetaldehyde (4.2 g., 0.02 mole) in a solution of sodium bisulfate (2.1 g., 0.02 mole) in 10 ml. of water. The mixture is warmed on a steam bath for 8 hr., cooled and acidified with glacial acetic acid. The acidified mixture is extracted with ether, and the combined ether extracts sequentially washed with water, dilute sodium bicarbonate solution and brine and dried over magnesium sulfate. Concentration of the dried ethereal solution under reduced pressure provides 3-methyl-1-[4-[(1-methylethyl)thio]phenoxy]-3-nitro-2-butanol.

(d) 3-Amino-3-methyl-1-[4-[(1-methylethyl)thio]phenoxy]2-butanol. A solution of 3-methyl-1-[4-[(1-methylethyl)thio]phenoxy]3-nitro-2-butanol (2.5 g., 0.008 mole) in 100 ml. of ether is treated with lithium aluminum hydride (0.5 g., 0.013 mole). The mixture is stirred at 25° for a 4 hr. period, cooled and then hydrolyzed by the sequential addition of 0.5 ml. of water, 0.5 ml. of 15% sodium hydroxide solution, and 1.5 ml. of water. After stirring at room temperature for 1 hr., the solution is filtered and concentrated under reduced pressure to provide 3-amino-3-methyl-1-[4-[(1-methylethyl)thio]phenoxy]-2-butanol.

(e) 3-Methyl-1-[4-[(1-methylethyl)thio]phenoxy]-3(octylamino)-2-butanol Preparation. A solution of 3-amino-3-methyl-1-[4-[(1-methylethyl)thio]phenoxy]-2-butanol (2.0 g., 0.007 mole) in 60 ml. of isopropyl alcohol is treated with n-octanol (1.0 g., 0.008 mole) and sodium cyanoborohydride (1.0 g., 0.017 mole). After stirring at room temperature for a period of 16 hr., it is poured into water and the product extracted with ether. The ethereal extract is washed with water and brine and dried over magnesium sulfate. Concentration of the dried ethereal solution and conversion of the residual free base to the hydrochloride salt provides 3-methyl-1-[4-[(1-methylethyl)thio]phenoxy]-3-(octylamino)-2-butanol hydrochloride.

EXAMPLE 12

1-[4-[(1-Methylethyl)thio]-phenoxy]-3-(octylamino)-2-butanol

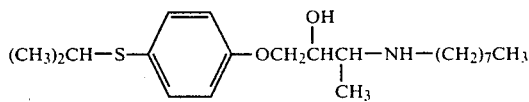

(a) 3-Amino-1-[4-[(1-methylethyl)thio]phenoxy]-2-butanol This amine precursor is obtained by reducing 1-[4-[(1-methylethyl)thio]phenoxy]-3-nitro-2-butanol with lithium aluminum hydride according to the procedure of Example 11(d). The nitro starting material (1-[4-[(1-methylethyl)thio]phenoxy]-3-nitro-2-butanol) is obtained by using an equivalent quantity of nitroethane in place of the 2-nitropropane in the procedure of Example 11(c).

(b) 1-[4-[(1-Methylethyl)thio]phenoxy]-3-octylamino-2-butanol Preparation. Treatment of 3-amino-1-[4-[(1-methylethyl)thio]phenoxy]-2-butanol with n-octanol and sodium cyanoborohydride according to the procedure of Example 11(e) affords the product 1-[4-[(1-methylethyl)thio]phenoxy]-3-octylamino-2-butanol.

EXAMPLES 13–28

The following compounds of Table A are prepared according to the procedure of Example 1 by reacting the epichlorohydrin derivative of the starting phenol with n-octylamine.

TABLE A $R_1-S-C_6H_4-OCH_2CHCH_2NH-(CH_2)_7CH_3$ (with OH on central carbon)

| Example | Starting Thiophenol | Product $R_1S$ |
| --- | --- | --- |
| 13 | 4-ethylthiophenol | 4-$C_2H_5$S |
| 14 | 4-n-propylthiophenol | 4-n-$C_3H_7$S |
| 15 | 4-n-butylthiophenol | 4-n-$C_4H_9$S |
| 16 | 4-n-pentylthiophenol | 4-n-$C_5H_{11}$S |
| 17 | 4-n-hexylthiophenol | 4-n-$C_6H_{13}$S |
| 18 | 4-n-heptylthiophenol | 4-n-$C_7H_{15}$S |
| 19 | 4-n-octylthiophenol | 4-n-$C_8H_{17}$S |
| 20 | 4-(3-methylbutylthio)phenol | 4-$(CH_3)_2CHCH_2CH_2$S |
| 21 | 2-n-butylthiophenol | 2-n-$C_4H_9$S |
| 22 | 3-n-butylthiophenol | 3-n-$C_4H_9$S |
| 23 | 2-ethylthiophenol | 2-$C_2H_5$S |
| 24 | 2-n-propylthiophenol | 2-n-$C_3H_7$S |
| 25 | 2-isopropylthiophenol | 2-i-$C_3H_7$S |
| 26 | 3-ethylthiophenol | 3-$C_2H_5$S |
| 27 | 3-n-propylthiophenol | 3-n-$C_3H_7$S |
| 28 | 3-isopropylthiophenol | 3-i-$C_3H_7$S |

EXAMPLE 29

Tablets

The following ingredients are blended into proportion by weight indicated according to conventional pharmaceutical techniques to provide a tablet base.

| Ingredient | Amount |
| --- | --- |
| Lactose | 79 |
| Corn Starch | 10 |
| Talcum | 6 |
| Tragancanth | 4 |
| Magnesium stearate | 1 |

This tablet base is blended with sufficient 1-[4-[(1-methylethyl)thio]phenoxy]-3-(octylamino)-2-propanol hydrochloride to provide tablets containing 10, 20, 40, 80, 160 and 320 mg. of active ingredient and compressed into conventional tablet press.

EXAMPLE 30

Dry-Filled Capsules

The following ingredients are blended in a conventional manner in the proportion by weight indicated.

| Ingredient | Amount |
| --- | --- |
| Lactose, U.S.P. | 50 |
| Starch | 5 |
| Magnesium stearate | 2 |

Sufficient 1-[4-[(1-methylethyl)thio]phenoxy]-3-(octylamino)-2-propanol hydrochloride is added to the blend to provide capsules containing 10, 20, 40, 80, 160 and 320 mg. of active ingredient which is filled into hard gelatin capsules of a suitable size.

EXAMPLE 31

Comparison of Peripheral Vasodilator Activity In The Anesthetized Dog

Test Method. Mongrol dogs of either sex weighing between 11 and 16 kg., each, were anesthetized with pentobarbital (30 mg./kg.) administered intravenously. The left brachial vein was cannulated and pentobarbital infused continuously throughout the experiment at a rate of 5 mg./kg./hr. A tracheotomy was performed and dogs ventilated mechanically with room air at a rate of 18 strokes/min. and a volume equivalent to 20 ml./kg. The vagi were sectioned bilaterally in the mid-cervical region of the neck. The right brachial vein and artery were cannulated to inject drugs and to monitor blood pressure via a Statham pressure transducer, respectively. All measurements were recorded on a Beckman-Offner dynograph. The abdominal aorta was exposed through midline incision and a loose ligature placed around the aorta distal to the left renal artery. The right (donor) and left (recipient) femoral arteries were exposed for cannulation and subsequent hind-limb perfusion. Following intravenous administration of heparin (5 mg/kg.) and gallamine triethiodide (2 mg./kg.), the right femoral artery was cannulated and the tip of the catheter advanced into the abdominal aorta to the level of the renal arteries. The left femoral artery was cannulated and the hind-limb perfused using a Harvard Perfusion pump. The ligature previously placed around the aorta was subsequently tied to minimize collateral circulation. Heparin and gallamine triethiodide were infused intravenously at rates of 2.5 and 1 mg./kg./hr., respectively. Perfusion pressure, measured at a point distal to the perfusion pump was set equal to 150 mm Hg. by adjusting pump speed. Blood flow to the limb was determined volumetrically at the conclusion of the experiment. The test agent was administered by infusion at a rate of from 0.1–1.0 mg./min. for a six-minute period and maximum reduction in pressure determined. One to three animals were employed per test agent.

Results. Table I below gives results obtained according to the above test for representative alkylthiophenoxypropanolamines of the instant invention. Data is also shown for the alkylthiophenoxypropanolamine prior art compounds of Keizer, et al., U.S. Pat. No. 3,542,874 "1-(isopropylamino)-3-[2-(methylthio)phenoxy]-2-propanol (tiprenolol)" and Villa, et al., Il. Farmaco. Sci., Ed. 24, 349–357 (1969) "1-(isopropylamino)-3-[4-(methylthio)phenoxy]-2-propanol" identified herein as test agents "A" and "B", respectively, and the reference standard papaverine.

With respect to prior art compounds "A" and "B" and the compound of Example 2 (test agent 2), comparative testing was repeated essentially as described above with the modification that the three compounds were tested in the same dog preparation (blood pressure was allowed to return to control values between infusion of test agents). This protocol precludes effects resulting from animal variation thus permitting a direct side-by-side comparison of vasodilating activity. The results of this comparison are also set forth in Table I.

TABLE I

Vasodilator Activity - Perfused Dog Hind Limb $$\text{R}_1\text{-S}-\text{C}_6\text{H}_3(\text{R})-\text{O}-\text{CH}_2\text{CHCH}_2\text{NH}-\text{R}_2$$
with OH on the central carbon

| Test Agent[a] | R | R₁ | R₂ | Pressure Decrease[b] Dose (mg./min.)[c] 0.3 | 1.0 |
|---|---|---|---|---|---|
| 1 | H | 4-CH₃ | n-C₈H₁₇ | −22 | −59 |
| 2 | H | 4-i-Pr | n-C₈H₁₇ | −44 −63[d] | −99 |
| 3 | H | 3-i-Pr | n-C₈H₁₇ | −20 | −87 |
| 5 | H | 4-i-Pr | (CH₂)₂—⟨⟩ | −63 | −87 |
| 6 | H | 4-i-Pr | (CH₂)₄—⟨⟩ | −47 | −74 |
| 7 | 2-CH₃ | 4-CH₃ | n-C₈H₁₇ | −56 | −80 |
| 8 | H | 2-CH₃ | n-C₈H₁₇ | −15 | −64 |
| A | H | 2-CH₃ | i-Pr | −20[d] | −27[d] |
| B | H | 4-CH₃ | i-Pr | −3[d] | −29[d] |
| Papaverine | | | | −31 | −55 |

[a]Test agent numbers correspond to example numbers.
[b]Millimeters of mercury.
[c]Infusion rate.
[d]Side-by-side comparison in same animals.

Findings Compared to prior art compuounds "A and B", all of the instant alkylthiophenoxypropanolamines tested (i.e. test agents 1–3 and 5–8) provided substantially greater vasodilating effects in that at an infusion dose of 1.0 mg./min. they produced a pressure reduction of from 59–99 mm Hg. whereas "A and B" at an identical dose provide a reduction in pressure of some 27–29 mm Hg. In comparison to prior art compounds "A and B" at a dose of 0.3 mg./min. the compounds tested were, respectively, from 0.8 to 3.2 and 5 to 21 times more active. All of the compounds tested are of interest with respect to vasodilator activity in that at an infusion rate of 1.0 mg./min. they produced a decrease in pressure substantially greater than or approximately equivalent to papaverine. According to the side-by-side comparison of test agent 2 and prior art alkylthiophenoxypropanolamines "A and B" at identical 0.3 mg./min. dose levels, test agent 2 has a vasodilator effect approximately 3.2 and 21 times greater than that of test agents "A" and "B", respectively. This illustrates that test agent 2 is a substantially superior vasodilator compared to the prior art alkylthiophenoxypropanolamine "A and B".

EXAMPLE 32

Inhibition of Platelet Aggregation (Antithrombogenic Activity)

Test Method. A method similar to that described in Born, Nature 194, 927 (1962) and O'Brien, J. Clinical Pathology 15, 446 (1962). This test comprises a nephelometric method in which the change in turbidity of a specimen of human platelet-rich plasma is measured on causation of platelet aggregation by addition of adenosine diphosphate (ADP) or collagen as the thrombogenic inducing agent. An increase in transmittance light occurs when the thrombogenic agent is added to the specimen of platelet-rich plasm due to clumping of platelets. Efficacy of the test compound is determined by ability to prevent the clumping and concomitant increase in transmittance. Various concentrations of the test agent are tested and that concentration causing a 50% reduction in the thrombogenic response is determined from a concentration-response curve.

Results. Table II below provides results obtained according to the above test for representative compounds of the instant invention and prior art compounds "A" and "B" of Example 31.

TABLE II

| Inhibition of Platelet Aggregation In Vitro Test Agent[a] | ED₅₀[b] ADP | Coll |
|---|---|---|
| 1 | 69 | 42 |
| 2 | 56 | 31 |
| 3 | 53 | 24 |
| 5 | 56 | 47 |
| 6 | 53 | 29 |
| 7 | 82 | 39 |
| 8 | 65 | 32 |
| A[c] | 137 | 33 |
| B[c] | 107 | 28 |

[a]Test agent numbers correspond to example numbers.
[b]Microgram/0.5 ml. platelet-rich human plasma when 1 mcg. of adenosine-5′-diphosphate (ADP) or the minimal amount of collagen (coll) producing maximal degree of aggregation are used to induce aggregation.
[c]Refer to Example 31.

Findings. The above data demonstrates that all of the compounds tested are significantly more active in inhibiting ADP-induced platelet aggregation than the prior art alkylthiophenoxypropanolamines "A" and "B".

EXAMPLE 33

Isolated Guinea Pig Trachea (beta-Adrenergic Blocking Activity)

Test Method. Tracheas excised from adult guinea pigs (body weight greater than 400 g.) are cut spirally and suspended vertically in 20 ml. of modified Tyrode's bath solution maintained at 37.5° C. and aerated continuously with oxygen. The lower end of a tracheal segment is fixed to a stationary glass rod and the upper end is threaded to an isometric tension transducer. Changes in the spontaneous tonus of the tracheal smooth muscle are monitored via the transducer and recorded continuously on an electronic recorder. Adrenergic beta-receptor blocking activity is determined by the ability of a test agent to inhibit the response of the isolated tissue to the adrenergic beta-stimulant "isoproterenol" at a concentration of 0.1 mcg./ml. bath fluid. The tissues are exposed to the test agent solution for a 15-min. interval prior to the addition of isoproterenol to the bath fluid. Beta-receptor blocking potency of a test drug is ascertained from concentration-response relationships wherein the response is expressed as a percent inhibition of isoproterenol-induced tissue response. The IC₅₀ value, which is the concentration of the test drug providing a 50% inhibition of the effect of the relaxant dose of isoproterenol, is determined by interpolation. Each drug solution is added to the tissue bathing medium at a constant volume of 0.2 ml./ml. of bath fluid and only one test drug concentration is employed for an individual tissue segment. Potency of the test agent relative to that of the beta-adrenergic blocking agent "propanolol" as a reference standard is assessed by comparing the IC₅₀ values.

Results. Table III below provides results obtained according to the above test for representative alkylthiophenoxypropanolamines of the instant invention identified by test number (example No.) compared to the alkylthiophenoxypropanolamine prior art compounds of Keizer, et al. supra. and Villa, et al. supra. referred to as test agents "A" and "B", respectively (consult Example 31 for chemical name).

TABLE III

Beta-Adrenergic Blocking Activity in the Isolated Guinea Pig Trachea $$R-\underset{R_1-S}{\underset{|}{\bigcirc}}-O-CH_2\underset{|}{\overset{OH}{C}}HCH_2NH-R_2$$

| Test Agent[a] | R | $R_1$ | $R_2$ | Beta-Adrenergic Blocking Potency[b] |
|---|---|---|---|---|
| 1 | H | 4-$CH_3$ | n-$C_8H_{17}$ | <0.001 |
| 2 | H | 4-i-Pr | n-$C_8H_{17}$ | <0.001 |
| 3 | H | 3-i-Pr | n-$C_8H_{17}$ | <0.001 |
| 4 | H | 4-i-Pr | n-$C_{12}H_{25}$ | <0.001 |
| 5 | H | 4-i-Pr | $(CH_2)_2$—⌬ | <0.0006 |
| 6 | H | 4-i-Pr | $(CH_2)_4$—⌬ | <0.002 |
| 7 | 2-$CH_3$ | 4-$CH_3$ | n-$C_8H_{17}$ | <0.0006 |
| 8 | H | 2-$CH_3$ | n-$C_8H_{17}$ | 0.004 |
| A[c] | H | 2-$CH_3$ | i-Pr | 1.0 |
| B[c] | H | 4-$CH_3$ | i-Pr | 0.2 |

[a]Test agent numbers correspond to example numbers.
[b]Potency relative to propanol (equals one) estimated from determinations of test drug concentrations causing 50% blockade of isoproterenol-induced tissue response (propanol $EC_{50}$ = 0.028 mcg./ml. bath fluid).
[c]Refer to Example 31.

Findings The data of Table III clearly establishes that, with respect to beta-adrenergic blocking activity, a marked distinction exists between the compounds of test agents 1 through 8 and the prior art alkylthiophenoxypropanolamines. It is apparent that test agents 1 through 8 are comparatively devoid of beta-adrenergic blocking activity in contrast to the corresponding prior art alkylthiophenoxypropanolamines "A" and "B" which have substantial activity. Consequently, the instant compounds when used for purposes described herein, would be relatively free of side effects associated with beta-adrenergic blocking activity.

EXAMPLE 34

Isolated Rabbit Thoracic Aorta (Antispasmodic Activity vs. Potassium Chloride)

Test Method. Antispasmodic activity was assessed in vitro by determining the effect of the test substance on induced contraction of arterial smooth muscle as follows. Adult, male, New Zealand White rabbits (body weight 2.5-4 kg.) were used. Each rabbit was killed by i.v. air injection. The thorax was opened and the descending thoracic aorta removed and placed in Kreb's-bicarbonate solution. Extraneous tissue was removed and the aorta was cut spirally along its entire length. Four spiral segments, each approximately 2 cm. in length (unstretched), were obtained from each thoracic aorta. A spiral segment was placed in a 10 ml. volume bath chamber, fixed at the lower end to a glass rod tissue holder, and the upper, free end threaded to a tension transducer which exerted a constant baseline tension of 3 gm on the tissue. The bath medium surrounding the aortic spiral (Kreb's-bicarbonate solution) was maintained at 37.5° C. and constantly aerated with 95% $O_2$:5% $CO_2$. Activity of the aortic smooth muscle was recorded on an electronic polygraph via its connection to the tension transducer. After an equilibration period of 60 min., a cumulative dose-response curve was obtained to an agonist (e.g. potassium chloride or norepinephrine) and the tissue then washed. Seventy-five min. later, a second cumulative dose-response curve to the agonist was obtained and the tissue washed again. Sixty min. later, a test drug solution was added to the tissue bath fluid and, after 15 min., drug exposure and, without washing, a third and final agonist-response curve was obtained. All additions to the bath fluid were 0.1 ml. volumes of aqueous solutions.

Results. Table IV below provides a comparison of potencies relative to papaverine in the above test employing potassium chloride as agonist for the instant alkylthiophenoxypropanolamines of Example 33 and prior art compounds of Keizer, et al., supra. ("A") and Villa, et al., supra. ("B") (consult Example 31 for chemical name). Papaverine is considered a direct-acting antispasmodic agent and is a standard in the art.

TABLE VI

Antispasmodic Activity (Rabbit Thoracic Aorta)

| Test Agent[a] | Antispasmodic Potency[b] |
|---|---|
| 1 | — |
| 2 | 0.6 |
| 3 | 0.7 |
| 4 | 0.08 |
| 5 | 2.4 |
| 6 | 0.02 |
| 7 | 0.8 |
| 8 | 2.6 |
| A[c] | 0.04 |
| B[c] | 0.04 |

[a]Test agent numbers correspond to example numbers.
[b]Potency relative to papaverine (equals one) estimated from $pA_2$ values determined versus potassium chloride-induced contractions. The $pA_2$ value represents the negative log of the molar concentration of the antagonist which reduces the effect of a double dose of agonist to that of a single dose of the agonist without the antagonist present.
[c]Refer to Example 31.

Findings. Antagonist activity against potassium chloride-induced spasms is indicative of non-adrenergic direct-acting antispasmodic action. Accordingly, the results set forth in Table IV illustrate that most of the instant compounds tested have a substantial level of antispasmodic activity whereas the prior art compounds "A" and "B" have relatively weak activity. The data further establishes that relative to potassium chloride-induced spasms, test agents 2, 3, 5, 7, and 8 are from about 15 to 65 times more potent as non-adrenergic antispasmodic agents than the corresponding prior art alkylthiophenoxypropanolamines "A" and "B". The antispasmodic potencies of test agents 4 and 6 are approximately the same as prior art compounds "A" and "B" with test agent 4 being twice as potent and test agent 6 being about ½ as potent.

EXAMPLE 35

Isolated Rabbit Thoracic Aorta (Antispasmodic Activity vs. Norepinephrine)

Test agents 1-8 and prior art compounds "A" and "B" of Example 34 were further tested for anti-alpha-adrenergic activity according to the method of Example 34 but employing the alpha-adrenergic stimulant agent norepinephrine as the agonist rather than potassium chloride. Selective activity against norepinephrine-induced spasms is indicative of alpha-adrenergic blocking (i.e. antispasmodic) activity. This modification of the antispasmodic test established that all of the instant alkylthiophenoxypropanolamines with exception of test agent 8, were essentially devoid of anti-alpha-adrenergic action having 0.3% or less of the activity exhibited by phentolamine. Phentolamine is an alpha-adrenergic blocking agent and a standard reference in the art. While prior art compound "B" is essentially inactive as an anti-alpha-adrenergic agent, test agent 8 and prior art compound "A" have somewhat more activity than compounds 1–7 in that they are 1–2% as potent as phentolamine. This experiment illustrates that the instant compounds are non-anti-alpha-adrenergic antispasmodic agents in that they have a substantial direct smooth muscle relaxant effect (as shown in Example 34) relatively uncomplicated by any significant selective alpha-adrenergic blocking effect.

EXAMPLE 36

Additional Biological Testing of 1-[4-[(1-Methylethyl)thio]phenoxy]-3-(octylamino)-2-propanol The above compound of Example 2 was further evaluated according to various pharmacological tests employed for that purpose. Thus:

(a) Rats with intra-arterial catheters have periods of shortened platelet survival time. This shortened survival time is normalized with the compound of Example 2.

(b) The compound of Example 2 elevated basal tone of mesenteric arteries of dogs and rabbits. This effect is considered valuable in the treatment of peripheral and cerebral vascular diseases.

(c) The compound of Example 2 decreased red blood cell rigidity determined via a chromium[51] labeling technique and accordingly the cells are better able to pass through sclerosed narrowed capillaries of tissues affected by vascular disease.

(d) The compound of Example 2 exhibited local anesthetic activity greater than, or as great as, that of lidocaine as determined by topical application to the rabbit eye or intradermal infiltration of guinea pig skin, respectively.

What is claimed is:

1. A compound of the formula

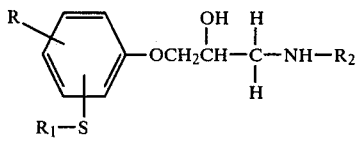

or an acid addition salt thereof wherein
R is hydrogen or methyl;
$R_1$ is alkyl of 1 to 4 carbon atoms inclusive;
$R_2$ is straight chain alkyl of 6 to 12 carbon atoms inclusive, or cyclohexylalkyl having 2 to 4 carbon atoms in the alkylene chain.

2. The compound according to claim 1 which is 1-[4-(methylthio)phenoxy]-3-(octylamino)-2-propanol or a non-toxic pharmaceutically acceptable acid addition salt thereof.

3. The compound according to claim 1 which is 1-[4-[(1-methylethyl)thio]phenoxy]-3-(octylamino)-2-propanol or a non-toxic pharmaceutically acceptable acid addition salt thereof.

4. The compound according to claim 1 which is 1-[4-[(methylethyl)thio]phenoxy]-3-(octylamino)-2-propanol hydrochloride.

5. The compound according to claim 1 which is 1-[3-[(1-methylethyl)thio]phenoxy]-3-(octylamino)-2-propanol or a non-toxic pharmaceutically acceptable acid addition salt thereof.

6. The compound according to claim 1 which is 1-[4-[(1-methylethyl)thio]phenoxy]-3-(dodecylamino)-2-propanol or a non-toxic pharmaceutically acceptable acid addition salt thereof.

7. The compound according to claim 1 which is 1-[(2-cyclohexylethyl)amino]-3-[4-[(1-methylethyl)thio]phenoxy]-2-propanol or a non-toxic pharmaceutically acceptable acid addition salt thereof.

8. The compound according to claim 1 which is 1-[(4-cyclohexylbutyl)amino]-3-[4-[(1-methylethyl)thio]phenoxy]-2-propanol or a non-toxic pharmaceutically acceptable acid addition salt thereof.

9. The compound according to claim 1 which is 1-[2-methyl-4-(methylthio)phenoxy]-3-(octylamino)-2-propanol or a non-toxic pharmaceutically acceptable acid addition salt thereof.

10. The compound according to claim 1 which is 1-[2-(methylthio)phenoxy]-3-(octylamino)-2-propanol or a non-toxic pharmaceutically acceptable acid addition salt thereof.

11. The therapeutic process for treating a mammal requiring vasodilation which comprises administering to said mammal an effective vasodilating amount of a compound as claimed in claim 1.

12. The process of claim 11 wherein said compound is 1-[4-[(1-methylethyl)thio]phenoxy]-3-(octylamino)-2-propanol.

13. The process of claim 11 wherein said compound is 1-[4-[(1-methylethyl)thio]phenoxy]-3-(octylamino)-2-propanol hydrochloride.

14. A pharmaceutical composition in dosage unit form comprising a pharmaceutically acceptable carrier in combination with an effective vasodilator amount of a compound of the formula

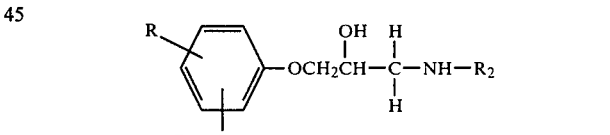

or an acid addition salt thereof wherein
R is hydrogen or methyl;
$R_1$ is alkyl of 1 to 4 carbon atoms inclusive;
$R_2$ is straight chain alkyl of 6 to 12 carbon atoms inclusive or cyclohexylalkyl having 2 to 4 carbon atoms in the alkylene chain.

15. The composition of claim 14 in which the active ingredient is 1-[4-[(1-methylethyl)thio]phenoxy]-3-(octylamino)-2-propanol.

* * * * *

REEXAMINATION CERTIFICATE (386th)

United States Patent [19]

Morrow et al.

[11] B1 4,243,681

[45] Certificate Issued Sep. 10, 1985

[54] ALKYLTHIOPHENOXYPROPANOLA-MINES AND PHARMACEUTICAL COMPOSITIONS AND USES THEREOF

[75] Inventors: Duane F. Morrow; William L. Matier, both of Evansville, Ind.

[73] Assignee: Mead Johnson & Company, Evansville, Ind.

Reexamination Request:
No. 90/000,381, May 11, 1983

Reexamination Certificate for:
Patent No.: 4,243,681
Issued: Jan. 6, 1981
Appl. No.: 30,497
Filed: Apr. 16, 1979

Related U.S. Application Data

[63] Continuation-in-part of Ser. No. 942,222, Sep. 14, 1978, abandoned, which is a continuation-in-part of Ser. No. 841,168, Oct. 11, 1977, abandoned.

[51] Int. Cl.$^3$ .................. A61K 31/135; C07C 83/00; C07C 91/00; C07C 93/06

[52] U.S. Cl. .................. 514/653; 260/501.17; 564/349

[58] Field of Search .................. 514/653; 260/501.17; 564/349

[56] References Cited

FOREIGN PATENT DOCUMENTS 1390748  4/1975  United Kingdom .

OTHER PUBLICATIONS

Experientia 23 (8) p. 651 (1967)–Wilhelm et al. (with translation).

*Primary Examiner*—Douglas W. Robinson

[57] ABSTRACT

A new class of alkylthiophenoxypropanolamine derivatives and methods for preparation are described. The compounds have vasodilating and antispasmodic activity, inhibit blood platlet aggregation and are substantially free of beta-adrenergic blocking effects. They are particularly valuable in the treatment of disease states responsive to vasodilation such as obstructive peripheral vascular diseases and cerebral vascular deficiencies. A representative and preferred embodiment of the invention consists of 1-[4-(1-methylethylthio)phenoxy]-3-octylamino)-2-propanol.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-15 is confirmed.

* * * * *